United States Patent
Desai et al.

(10) Patent No.: US 7,402,594 B2
(45) Date of Patent: Jul. 22, 2008

(54) SULFATED BIS-CYCLIC AGENTS

(75) Inventors: Umesh R. Desai, Mechanicsville, VA (US); Gunnar Gunnarsson, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 112 days.

(21) Appl. No.: 10/556,906

(22) PCT Filed: May 19, 2004

(86) PCT No.: PCT/US2004/015731

§ 371 (c)(1),
(2), (4) Date: Sep. 26, 2006

(87) PCT Pub. No.: WO2004/103961

PCT Pub. Date: Dec. 2, 2004

(65) Prior Publication Data

US 2007/0173529 A1    Jul. 26, 2007

(51) Int. Cl.
C07D 217/04    (2006.01)
A61K 31/47    (2006.01)
(52) U.S. Cl. .................. 514/307; 546/139; 546/146
(58) Field of Classification Search .......... 546/139, 546/146; 514/307
See application file for complete search history.

(56) References Cited

U.S. PATENT DOCUMENTS 5,578,729 A * 11/1996 Bringmann et al. ......... 546/140
6,849,644 B2 * 2/2005 Bromidge et al. .......... 514/307

OTHER PUBLICATIONS

Gunnarsson et al., "Designing Small, Nonsugar Activators of Antithrombin Using Hydrophathic Interaction Analyses", J. Med. Chem, 2000 vol. 45, pp. 1233-1243.
Gannarsson et al., Interaction of designed Sulfated Falvanoids with Antithrombin: Lessons on the Design of Organic Activators; J. Med. Chem,; 2002, vol. 45, pp. 4460-4470.

* cited by examiner

*Primary Examiner*—Zinna N Davis
(74) *Attorney, Agent, or Firm*—Whitham Curtis Christofferson & Cook, PC

(57) ABSTRACT

Sulfated bis-cyclic compounds that are potent anticoagulants and methods for their manufacture are provided. The sulfated compounds are bis-cyclic moieties comprised of an isoquinoline ring joined to a phenyl ring with the general chemical structure formula (I) where $R_2$ is hydrogen or a sulfate moiety, $R_3$ is either hydrogen or carboxylate moiety; $R_4$ is a hydrogen or oxygen; and $R_5$ is a hydrogen if $R_4$ is a hydrogen, and is absent if $R_4$ is oxygen. Counterions such as sodium may also be coordinated to the sulfate and carboxylate moieties.

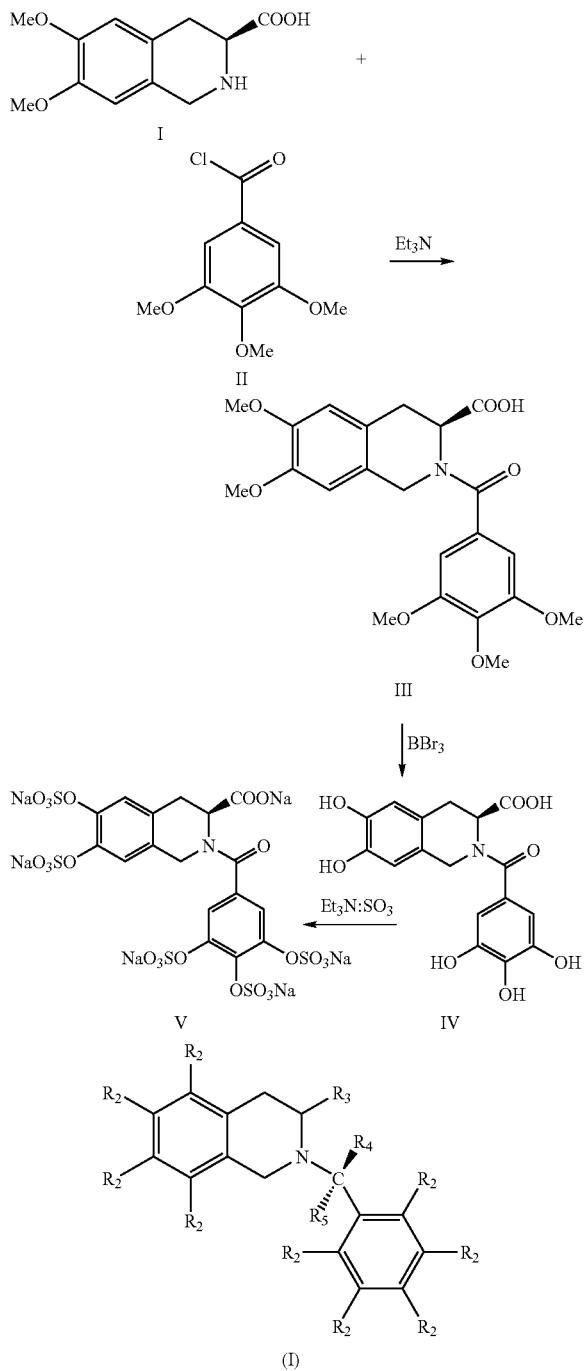

15 Claims, 3 Drawing Sheets

SULFATED BIS-CYCLIC AGENTS

BACKGROUND OF THE INVENTION

1. Field of the Invention

The present invention generally relates to anticoagulants. More particularly, the invention provides sulfated bis-cyclic compounds that mimic the anticoagulant function of heparin.

2. Background Description

Heparin is widely used as an anticoagulant in the treatment of conditions requiring such an agent, e.g. as a "blood thinner" prior to invasive cardiac surgical procedures. Heparin is a linear co-polymer composed of alternating glucosamine and uronic acid residues. A heparin chain may contain anywhere from ~10 to ~80 of these saccharide residues, thus making a typical heparin preparation polydisperse. Further, these saccharide residues may be sulfated at various positions, thus making a typical heparin chain heterogeneous.

Commercially available heparin is a natural product obtained from either bovine or porcine sources (1). A commercial heparin preparation is thus a mixture of numerous polysaccharide species of different chain lengths and sulfate group distributions. Low-molecular-weight heparins (LMWH) have been prepared from the natural product through both enzymatic and chemical means. These heparins are preparations in which the average molecular weight of the parent polysaccharide has been selectively reduced from ~14,000 to ~5,000. However, LMWHs are still heterogenous and polydisperse. Further, while LMWH are in general structurally similar to parent heparin, they may contain chemical changes introduced by the method of preparation.

Thus, one drawback in the use of heparin or LMWH for clinical purposes is that, due to their inherent polydisperse and heterogeneous nature, commercial preparations for clinical administration are relatively ill-defined. As a result, attempts have been made to design and produce heparin replacements with defined compositions. For example, a specific pentasaccharide that mimics the action of heparin and LMWH is available. This pentasaccharide is a linear molecule consisting of 1→4 linked glucoamine and uronic acid residues that are sulfated at specific points. The pentasaccharide is obtained through chemical synthesis (2). Unfortunately, the synthesis of the pentasaccharide is a multi-step, intricate and low-yielding procedure. Similarly, small, non-sugar molecules that partially mimic the anticoagulant action of heparin have been described in the literature. These molecules belong to either the flavan or the flavone series of structures, and are sulfated flavan or flavone derivatives (3). However, these products also fail to exhibit the highly efficient anticoagulant properties of heparin (4).

The prior art has heretofore failed to provide an anticoagulant of defined composition that is as effective as heparin and conveniently obtained. There is thus an ongoing need to develop such alternative anticoagulant agents.

SUMMARY OF THE INVENTION

It is an object of the present invention to provide a new class of sulfated compounds that exhibit potent anticoagulant activity. Synthesis of the compounds is relatively straightforward and economical and results in a homogeneous, monodisperse product of defined composition. In fact, the sulfated compounds of the present invention can be synthesized in only three sequential steps from commercially available chemicals.

The sulfated compounds of the present invention are bis-cyclic moieties comprised of a phenyl ring joined to an isoquinoline ring, as depicted in the following chemical structure:

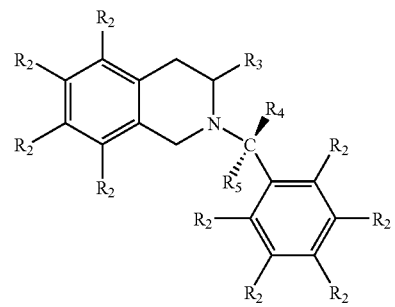

The sulfated compound may further comprise at least one cation or cationic group such as sodium, potassium, ammonium, tetraalkylammonium, etc. In the family of compounds, $R_2$ may be hydrogen or a sulfate moiety, and may be the same or different at each location, provided that at least one location (i.e., one $R_2$) is a sulfate ($OSO_3^-$) moiety. $R_3$ is either hydrogen or carboxylate moiety; $R_4$ is a hydrogen or oxygen (e.g. of a ketone moiety); and $R_5$ is a hydrogen if $R_4$ is a hydrogen, and is absent if $R_4$ is oxygen. The sulfate moieties may include (i.e. be coordinated to or ionically bonded to) a cation such as a sodium, potassium, ammonium, or tetraalkylammonium cation.

In one embodiment, $R_3$ is hydrogen. In another embodiment, $R_3$ is a carboxylate moiety. The carboxylate moiety may include (i.e. be coordinated to or ionically bonded to) a cation such as a sodium, potassium, or ammonium cation.

In one embodiment of the invention, at least two of $R_2$ are sulfate moieties. In another embodiment, at least three of $R_2$ are sulfate moieties. In a third embodiment of the invention, at least four of $R_2$ are sulfate moieties, and in a fourth embodiment, at least five of $R_2$ are sulfate moieties.

Examples of such compounds include:

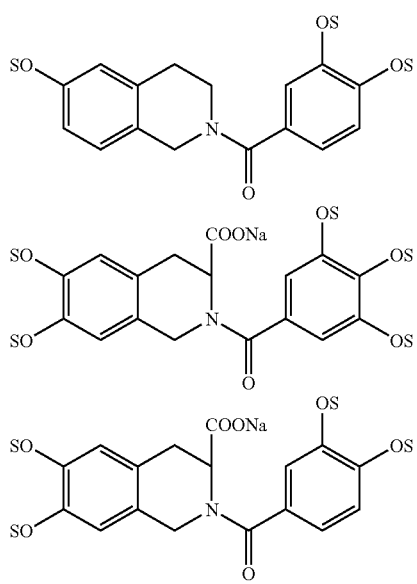

-continued

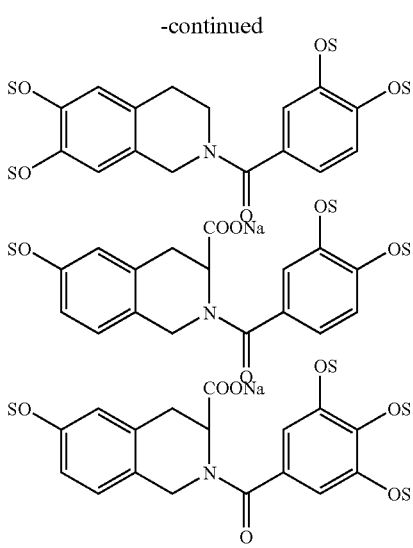

where S stands for [$SO_3^-$] ionically bonded to either sodium, potassium, ammonium or tetraalkylammonium cation.

DETAILED DESCRIPTION OF THE PREFERRED EMBODIMENTS OF THE INVENTION

Figure 1:
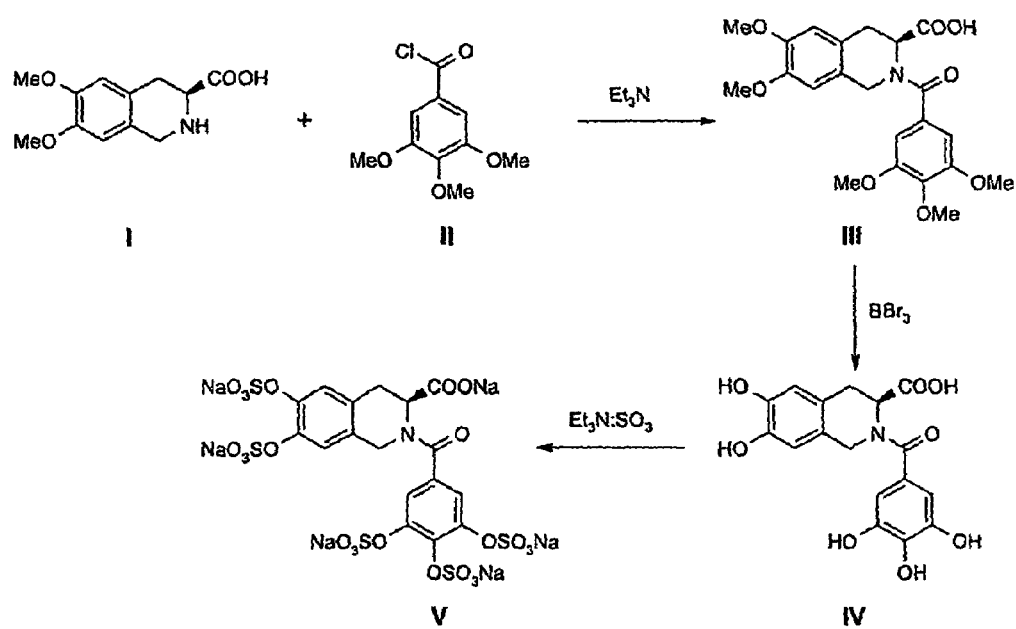
FIG. 1. Synthesis scheme for polysulfonated compounds.

The present invention provides a new class of sulfated compounds that exhibit potent anticoagulant activity. Synthesis of the compounds is relatively straightforward and economical and results in a homogeneous, monodisperse product of defined composition. In fact, the sulfated compounds of the present invention can be synthesized in only three sequential steps from commercially available chemicals.

The sulfated compounds of the present invention are biscyclic moieties comprised of an isoquinoline ring joined to a phenyl ring by a chemical group that is two bonds long. A representative generic structure is

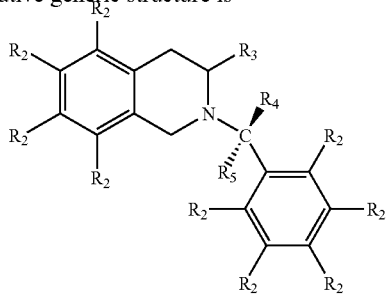

The chemical group that forms the two-bond long connection between the isoquinoline ring and the phenyl ring may be an alkyl group (e.g. $CH_2$ where $R_4$ and $R_5$ are both H) or a carbonyl group (e.g. CO where $R_4$ is O and $R_5$ is absent). Those skilled in the art will recognize that if the connecting chemical group is alkyl, the central carbon will be tetravalent and display the geometry depicted in Formula 1 (or the stereoisomer in which $R_4$ is "behind the plane" and $R_5$ is "out of the plane). However, if $R_4$ represents O of a carbonyl function and $R_5$ is absent, then the central carbon displays characteristic "flat" trigonal geometry.

The isoquinoline ring contains heterocyclic nitrogen at position 2 and may be substituted or unsubstituted with a carboxylate at position 3 ($R_3$). The $R_2$ positions on the isoquinoline ring may be unsubstituted or substituted with sulfate moieties, i.e. $OSO_3^-$. Likewise, the phenyl ring may be unsubstituted or substituted with one or more sulfates at the $R_2$ positions, with the caveat that at least one sulfate moiety must be substituted on the molecule as a whole.

The compounds of the present invention may further contain suitable positively charged counterions to balance the negative charge of substituted moieties on the compound. As described above, the substituted moieties are sulfate ($OSO_3^-$) or, in the case of $R_3$, carboxylate ($COO^-$). Those skilled in the art will recognize that these moieties will bear a negative charge under certain conditions, (e.g. at appropriate values of pH, concentration, ionic strength, and temperature) and thus the compounds may form salts, i.e. suitable cations or cationic groups may be coordinated to (ionically bonded to) them. Examples of suitable counterions include but are not limited to sodium ($Na^+$), potassium ($K^+$), ammonium ($NH_4^+$) and tetraalkylammonium ($NR_4^+$).

The present invention also encompasses a pharmaceutical preparation comprising at least one compound of the present invention. The compounds of the invention can be used either as the free base or as the pharmaceutically acceptable acid-addition salt form, for example, hydrochloride, hydrobromide, tartrate, and maleate. Such a pharmaceutical preparation may be in any of many forms suitable for administration of drugs, including but not limited to injectable dosage forms and solid dosage forms such as tablets, capsules, and the like. The compounds can be administered in the pure form or in a pharmaceutically acceptable formulation including suitable elixirs, binders, and the like, or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of 1-99% of the composition and the vehicular "carrier" will constitute 1-99% of the composition. The pharmaceutical compositions of the present invention may include any suitable pharmaceutically acceptable additives or adjuncts to the extent that they do not hinder or interfere with the therapeutic effect desired of agent. As can be seen from the experiments below, the compounds may be used as an anticoagulant. Furthermore, the compounds may be used extracorporeal for anticoagulant activity.

Those of skill in the art will recognize that the exact dosage of an agent to be administered may vary depending on factors such as the age, gender, weight and overall health status of the individual patient, as well as on the nature of the disorder being treated. Generally, dosages in the range of from about 0.1 to about 1000 mg active agent/kg body weight/24 hr., and more preferably about 1.0 to about 500.0 mg active agent/kg body weight/24 hr., and even more preferably about 10 to about 100.0 mg active agent/kg body weight/24 hr., are effective. The level of efficacy and optimal amount of dosage for any given compound may vary from compound to compound.

The agents of the present invention may be administered by any of a wide variety of means which are well known to those of skill in the art, (including but not limited to intravenously, intramuscularly, intraperitoneally, orally, rectally, intraocularly, and the like) or by other routes (e.g. transdermal, sublingual, aerosol, etc.). and may be in any form (e.g. liquid, solid, etc.) which is suitable for the means of administration. Further, the agents may be administered either alone or together with other medications in a treatment protocol, or may be used extracorporeally.

The anticoagulant compounds of the present invention may have a variety of clinical applications. Such applications include but are not limited to: the treatment of patients in need of an anti-coagulant for any reason, such as to prevent blood clotting or to increase clotting times prior to, during or after heart (or other) surgeries; for treatment (dissolution) of established clots; for prevention of clots in those thought to be at risk for their development for any reason; etc. Further, the compounds may also have value in a clinical diagnostic setting, e.g. to prevent or slow clotting during assays in which it is desirable to do so. In addition, the compounds may be utilized in a research setting in which it is desired to prevent or slow the clotting process.

EXAMPLES

Methods. To assay anticoagulant activity, compounds were incubated with 1 µM human plasma antithrombin and 10 nM human plasma factor Xa in 20 mM sodium phosphate buffer, pH 6.0, at 25° C. for 10 min. After incubation, residual factor Xa activity was measured spectrophotometrically using Spectrozyme fXa substrate. From the decrease in residual factor Xa activity as a function of sulfated bis-cyclic agent concentration, the anticoagulant potential of each sample was calculated.

Example 1

Synthesis of Polysulfated Compounds

The polysulfated compounds are synthesized as a mixture followed by chromatography to isolate individual molecules. Referring to FIG. 1, first, a methoxy-substituted isoquinoline, e.g., I, is made to react with a methoxy-substituted benzoyl chloride, e.g., II under basic conditions to obtain the methoxy-substituted bis-cyclic agent, e.g., III. This reaction is performed under anhydrous conditions at room temperature or lower to obtain in quantitative yield product III. The bis-cyclic agent is then made to react with boron tribromide in carbon tetrachloride at −20° C. to deprotect the methoxy groups and obtain IV.

The multi-phenol IV so obtained is then sulfated with triethylamine-sulfur trioxide complex at 65° C. in dimethylacetamide to obtain the polysulfated bis-cyclic agent V. The reaction is allowed to proceed for overnight under anhydrous conditions in nitrogen atmosphere. Some coloring of the reaction mixture is observed. The reaction mixture is poured in acetone and the solution allowed to stand at 4° C. for 24 h. The colored oil deposited at the bottom is collected, dissolved in 30% (w/v) sodium acetate and precipitated by dropwise addition of 100% ethanol. Precipitates are collected by filtration. These precipitates contain a mixture of compounds with varying degrees of sulfation.

Example 2

Separation of Mixture into Fractions with Differing Sulfate Groups

The mixture obtained in Example 1 includes compounds that are differentially sulfated at the substitution sites. The mixture is separated into individual components using traditional gel-filtration and weak anion-exchange chromatography. This mixture is passed through a gel-filtration column that resolves molecules in the range of MW 200-1,000 to yield several fractions (e.g. F1 through F5, FIG. 2A).

Figure 2:
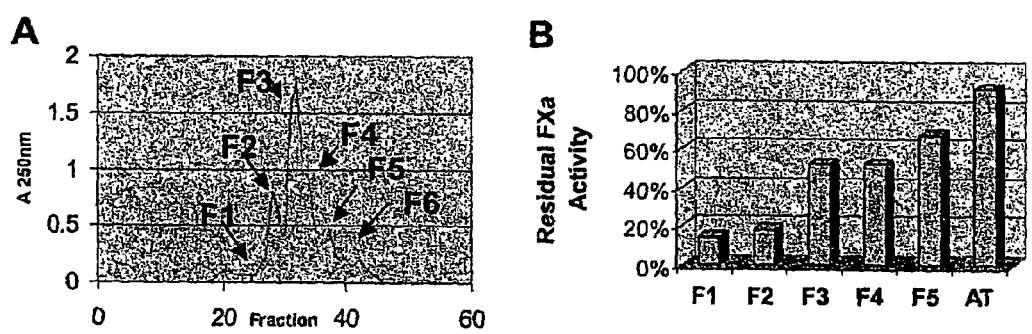
FIGS. 2A and B. Results of gel-filtration column analysis. A, y axis, absorbance at 250 nm, x axis, fraction number. B, residual Fxa activity per fraction.

A key test of in vitro anticoagulant activity is the inhibition of Factor Xa., a critical enzyme involved in blood clotting. This enzyme is central to the overall phenomenon of clot formation and the heparin pentasaccharide that is clinically available as an anticoagulant primarily inhibits this enzyme to exert its therapeutic effect. Biochemical analysis of fractions F1 through F5 for inhibition of antithrombin-dependent factor Xa activity showed that fraction F1 exhibited the highest inhibition, and that inhibition progressively decreases through F5 (FIG. 2B). Fraction 6 was inactive and hence was not considered further.

This example demonstrates that the series of bis-cyclic compounds with differing numbers of sulfate groups inhibit a critical enzyme factor Xa of the blood coagulation cascade.

Example 3

Anticoagulant Activity Testing

Figure 3:
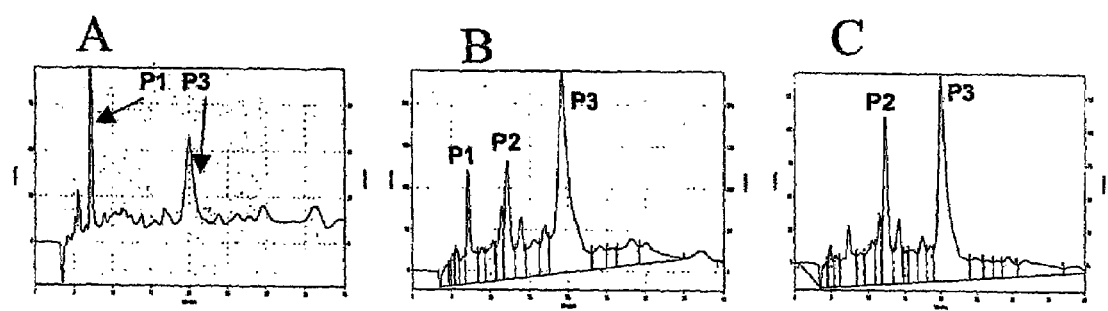
FIG. 3A-C. Purification using DEAE-anion exchange column of fractions obtained via gel-filtration. A, results obtained for fraction F1; B, results obtained for fractions F2; results obtained for fraction F3.

Each fraction obtained as in Example 2 was further purified on DEAE-anion exchange column. The results for fractions F1, F2 and F3 are shown in FIGS. 3A, 3B and 3C, respectively. As can be seen, Fraction 1 yields two major peaks, P1 and P3; Fraction F2 yields three major peaks P1, P2 and P3; and Fraction F3 yields two major peaks, P2 and. P3. Chemical analysis of peaks P1, P2 and P3 indicate that peak P1 is the fully sulfated molecule, (3S)-6,7-bis-sulfonato-2-(3,4,5-tris-sulfonato-benzoyl)-1,2,3,4-tetrahydro-isoquinoline-3-carboxylate, while peaks P2 and P3 have one or two less sulfate groups, respectively, either in the isoquinoline or the phenyl ring system.

Each peak was isolated and its factor Xa inhibition potential was determined at concentrations in the range of 1-50 µM. The results at 10 µM concentration of sulfated compound are given in Table 1. The date show that the pentasulfated bis-cyclic molecule ((3S)-6,7-bis-sulfonato-2-(3,4,5-tris-sulfonato-benzoyl)-1,2,3,4-tetrahydro-isoquinolne-3-carboxylate) greatly accelerates the inhibition of human factor Xa by human plasma antithrombin.

TABLE 1

Factor Xa inhibition by sulfated compounds

| Agent | Inhibition |
|---|---|
| Antithrombin alone | 19% |
| Peak P3 (trisulfated) | 48% |
| Peak P2 (tetrasulfated) | 48% |
| Peak P1 (pentasulfated) | 86% |

This example demonstrates that bis-cyclic sulfated molecules as described herein possess excellent anticoagulant properties.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

1. Linhardt, R. J. (1991) Heparin: An important drug enters its seventh decade. *Chem. Ind.* 2, 45-50.
2. van Boeckel, C. A. A. and Petitou, M. (1993) The unique antithrombin III binding domain of heparin: A lead to new synthetic antithrombotics. *Angew. Chem. Int. Ed. Engl.* 32, 1671-1818.
3. Gunnarsson, G. T. and Desai, U. R. (2002) Designing small, non-sugar activators of antithrombin using hydropathic interaction analyses. *J. Med. Chem.* 45, 1233-1243.
4. Gunnarsson, G. T. and Desai, U. R. (2002) Interaction of sulfated flavanoids with antithrombin: Lessons on the design of organic activators. *J. Med. Chem.* 45, 4460-4470.

The invention claimed is:

1. A sulfated compound having the chemical structure:

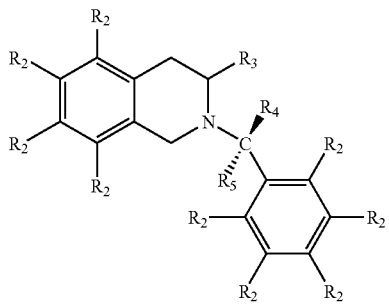

wherein
$R_2$ is selected from the group consisting of hydrogen and sulfate moieties, and may be the same or different at each location, provided that at least one location is a sulfate moiety, and
$R_3$ is selected from the group consisting of hydrogen and a carboxylate moiety,
$R_4$ is a hydrogen or oxygen, and
$R_5$ is a hydrogen if $R_4$ is a hydrogen, and is absent if $R_4$ is oxygen.

2. The sulfated compound of claim 1 further comprising at least one cation or cationic group selected from the group consisting of sodium, potassium, ammonium, and tetraalkylammonium.

3. The sulfated compound of claim 1 wherein $R_3$ is hydrogen.

4. The sulfated compound of claim 1 wherein $R_3$ is a carboxylate moiety.

5. The sulfated compound of claim 1 wherein at least two of $R_2$ are sulfate moieties.

6. The sulfated compound of claim 1 wherein at least three of $R_2$ are sulfate moieties.

7. The sulfated compound of claim 1 wherein at least four of $R_2$ are sulfate moieties.

8. The sulfated compound of claim 1 wherein at least five of $R_2$ are sulfate moieties.

9. The sulfated compound of claim 1 wherein at least one of $R_2$ on a phenyl ring and at least one of R2 on an isoquinoline ring is a sulfate moiety.

10. The sulfated compound of claim 1 wherein $R_4$ is oxygen of a carbonyl and $R_5$ is absent.

11. The sulfated compound of claim 1 wherein $R_4$ and $R_5$ are hydrogen.

12. The sulfated compound of claim 1 having a chemical structure selected from the group consisting of:

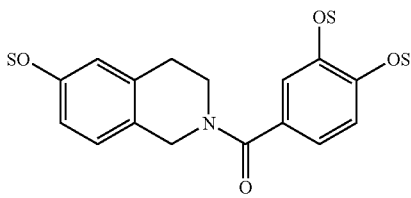

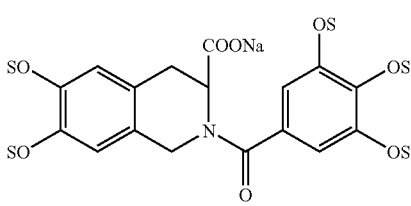

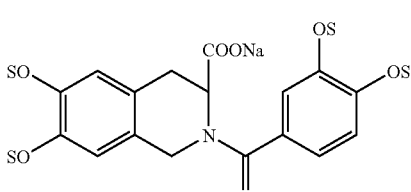

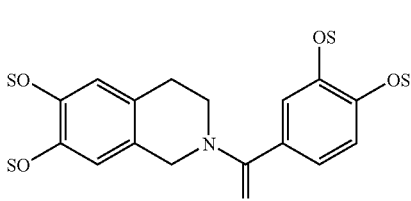

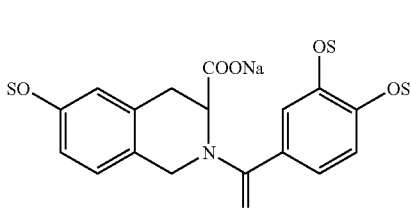

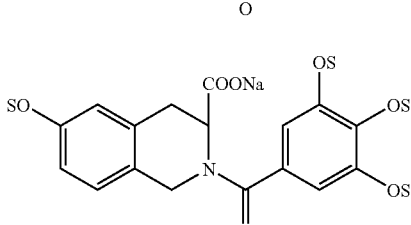

13. An anticoagulation method comprising the step of exposing blood or a component thereof to a compound having the chemical structure:

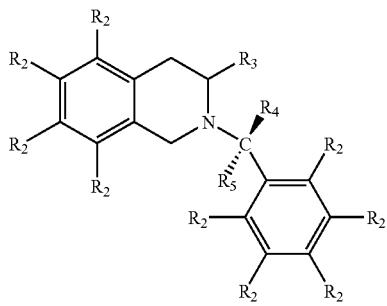

wherein
  $R_2$ is selected from the group consisting of hydrogen and sulfate moieties, and may be the same or different at each location, provided that at least one location is a sulfate moiety, and
  $R_3$ is selected from the group consisting of hydrogen and a carboxylate moiety,
  $R_4$ is a hydrogen or oxygen, and
  $R_5$ is a hydrogen if $R_4$ is a hydrogen, and is absent if $R_4$ is oxygen.

14. The method of claim 13 wherein the exposing step is performed extracorporeal.

15. The method of claim 13 wherein $R_4$ is an oxygen.

* * * * *